United States Patent [19]
Weathers

[11] Patent Number: 6,020,005
[45] Date of Patent: Feb. 1, 2000

[54] GENITAL WART TREATMENT

[76] Inventor: Ervin G. Weathers, 8624 Hwy. 238, Jacksonville, Oreg. 97530

[21] Appl. No.: 09/288,127

[22] Filed: Apr. 8, 1999

[51] Int. Cl.[7] ............................ A61K 33/32; A61K 33/06
[52] U.S. Cl. .......................... 424/640; 514/827; 514/828; 514/887; 514/931; 514/932; 514/933; 514/934; 424/698
[58] Field of Search .................................. 424/640, 698; 514/827, 828, 887, 931–934

[56] References Cited

U.S. PATENT DOCUMENTS

| | | | |
|---|---|---|---|
| 3,467,747 | 9/1969 | Hammarskjold et al. | 514/161 |
| 4,016,264 | 4/1977 | Clark | 514/141 |
| 4,055,660 | 10/1977 | Meierhenry | 514/535 |
| 4,801,444 | 1/1989 | Kravchenko | 424/45 |
| 5,476,664 | 12/1995 | Robinson et al. | 424/443 |
| 5,767,135 | 6/1998 | Fernandez-Pol | 514/354 |

OTHER PUBLICATIONS

Martindale The Extra Pharmacopoeia, 13th ed., The Pharmaceutical Press, London, 1993, pp. 803,1759 (last column, see entries for "Permantasico" and "Permitabs."
Embase abstract, Accession No. 85207296 (1985).
Embase abstract, Accession No. 76206705 (1975).

*Primary Examiner*—John Pak

[57] ABSTRACT

A genital wart treatment for treating and removing genital warts. The genital wart treatment includes the acts of dissolving a volume of particulate potassium permanganate in a volume of water to form a treatment solution, and repeatedly performing over a duration of time a treatment application comprising the acts of applying the treatment solution on to genital warts and surrounding skin of a subject to wet the genital warts and surrounding skin with the treatment solution, applying a styptic to the wet genital warts and surrounding skin, and then removing an outermost layer of skin on the genital warts.

9 Claims, No Drawings

GENITAL WART TREATMENT

BACKGROUND OF THE INVENTION

1. Field of the Invention

The present invention relates to genital wart treatments and more particularly pertains to a new genital wart treatment for treating and removing genital warts.

2. Description of the Prior Art

Genital wart treatments are known in the prior art. More specifically, genital wart treatments heretofore devised and utilized are known to consist basically of familiar, expected and obvious treatments, notwithstanding the myriad of method encompassed by the crowded prior art which have been developed for the fulfillment of countless objectives and requirements.

Known prior art includes U.S. Pat. No. 5,767,135; U.S. Pat. No. 4,055,660; U.S. Pat. No. 4,016,264; U.S. Pat. No. 3,948,265; U.S. Pat. No. 5,476,664; and U.S. Pat. No. 3,467,747.

SUMMARY OF THE INVENTION

In view of the foregoing disadvantages inherent in the known types of genital wart treatments now present in the prior art, the present invention provides a new genital wart treatment which can be utilized for treating and removing genital warts.

The general purpose of the present invention, which will be described subsequently in greater detail, is to provide a new genital wart treatment method which has many of the advantages of the genital wart treatments mentioned heretofore and many novel features that result in a new genital wart treatment which is not anticipated, rendered obvious, suggested, or even implied by any of the prior art genital wart treatments, either alone or in any combination thereof.

To attain this, the present invention generally comprises the acts of dissolving a volume of particulate potassium permanganate in a volume of water to form a treatment solution, and repeatedly performing over a duration of time a treatment application comprising the acts of applying the treatment solution on to genital warts and surrounding skin of a subject to wet the genital warts and surrounding skin with the treatment solution, applying a styptic to the wet genital warts and surrounding skin, and then removing an outermost layer of skin on the genital warts.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new genital wart treatment method which has many of the advantages of the genital wart treatments mentioned heretofore and many novel features that result in a new genital wart treatment which is not anticipated, rendered obvious, suggested, or even implied by any of the prior art genital wart treatments, either alone or in any combination thereof.

It is another object of the present invention to provide a new genital wart treatment which may be easily and efficiently marketed.

It is a further object of the present invention to provide a new genital wart treatment which is reliable.

An even further object of the present invention is to provide a new genital wart treatment which is susceptible of a low cost of manufacture with regard to both materials and labor, and which accordingly is then susceptible of low prices of sale to the consuming public, thereby making such genital wart treatment economically available to the buying public.

Still yet another object of the present invention is to provide a new genital wart treatment which provides in the methods of the prior art some of the advantages thereof, while simultaneously overcoming some of the disadvantages normally associated therewith.

Still another object of the present invention is to provide a new genital wart treatment for treating and removing genital warts.

Yet another object of the present invention is to provide a new genital wart treatment which includes the acts of dissolving a volume of particulate potassium permanganate in a volume of water to form a treatment solution, and repeatedly performing over a duration of time a treatment application comprising the acts of applying the treatment solution on to genital warts and surrounding skin of a subject to wet the genital warts and surrounding skin with the treatment solution, applying a styptic to the wet genital warts and surrounding skin, and then removing an outermost layer of skin on the genital warts.

Still yet another object of the present invention is to provide a new genital wart treatment that provides a painless and permanent means for removing genital warts.

These together with other objects of the invention, along with the various features of novelty which characterize the invention, are pointed out with particularity in the claims annexed to and forming a part of this disclosure.

DESCRIPTION OF THE PREFERRED EMBODIMENT

Generally, genital wart treatment generally comprises the acts of dissolving a volume of particulate potassium permanganate in a volume of water to form a treatment solution, and repeatedly performing over a duration of time a treatment application comprising the acts of applying the treatment solution on to genital warts and surrounding skin of a subject to wet the genital warts and surrounding skin with the treatment solution, applying a styptic to the wet genital warts and surrounding skin, and then removing an outermost layer of skin on the genital warts.

In closer detail, the method for treating genital warts on a patient or subject comprises the acts of first forming a treatment solution by dissolving a volume of particulate potassium permanganate in a volume of water. Preferably, the volume of potassium permanganate comprises about ½ teaspoon of potassium permanganate and the volume of water comprises about 1 cup of luke warm water.

Next, a treatment application is performed comprises the acts of first applying the treatment solution on to genital warts and surrounding skin of a subject (typically located on the penis, vagina, and anus of the subject) to wet the genital warts and surrounding skin of the subject with the treatment solution. Preferably, the treatment solutions is applied to the genital warts and surrounding skin of the subject by means of a misting spray device such as an atomizer. Second, a dry styptic is then applied to the entire wet area of genital warts and surrounding skin. Preferably, the styptic comprises a styptic pencil comprises alum. Third, the wet area of genital warts and surrounding skin is air dried. Fourth, after drying, a period time must pass, preferably between about three days and about four days. During this time, the genital warts will begin to have a dull or numb sensation and a thin layer of skin will begin to peel from the genital warts. Finally, after the period of time has elapsed, an outermost layer of skin on the genital warts may be removed preferably either with a toothpick or a wet washcloth.

The treatment application is repeated several times for a duration of time after the first treatment application until the genital warts are no longer present on the subject. Typically, the duration of time is between about two weeks and about four weeks.

As to a further discussion of the manner of usage and operation of the present invention, the same should be apparent from the above description. Accordingly, no further discussion relating to the manner of usage and operation will be provided.

Therefore, the foregoing is considered as illustrative only of the principles of the invention. Further, since numerous modifications and changes will readily occur to those skilled in the art, it is not desired to limit the invention to the exact operation described, and accordingly, all suitable modifications and equivalents may be resorted to, falling within the scope of the invention.

I claim:

1. A method for treating genital warts on a subject, comprising:
   (i) dissolving a volume of particulate potassium permanganate in a volume of water to form a treatment solution;
   (ii) performing a treatment application comprising the steps of:
       applying said treatment solution to genital warts and surrounding skin of a subject to wet the genital warts and surrounding skin with said treatment solution;
       applying a styptic to the wet genital warts and surrounding skin; and
       removing an outermost layer of skin on said genital warts; and
   (iii) repeating said treatment application for a duration of time until the genital warts are no longer present on the subject.

2. The method of claim 1, wherein said volume of potassium permanganate comprises about ½ teaspoon of potassium permanganate, wherein said volume of water comprises about 1 cup of water.

3. The method of claim 1, wherein said styptic comprises a styptic pencil.

4. The method of claim 1, wherein said treatment application further comprises the step of air drying the wet genital warts and surrounding skin and waiting a period of time to pass that is sufficient to provide a dull or numb sensation in the genital warts and peeling of a thin layer of skin from the genital warts after the step of applying a styptic to the wet genital warts and surrounding skin and before the step of removing an outermost layer of skin on said genital warts.

5. The method of claim 4, wherein said period of time is between about three days and about four days.

6. The method of claim 1, wherein said outermost layer of skin is removed with a toothpick.

7. The method of claim 1, wherein said outermost layer of skin is removed with a wet washcloth.

8. The method of claim 1, wherein said duration of time is between about two weeks and about four weeks.

9. A method for treating genital warts on a subject, comprising:
   (i) dissolving a volume of particulate potassium permanganate in a volume of water to form a treatment solution, wherein said volume of potassium permanganate comprises about ½ teaspoon of potassium permanganate, wherein said volume of water comprises about 1 cup of water;
   (ii) performing a treatment application comprising the steps of:
       applying said treatment solution to genital warts and surrounding skin of a subject to wet the genital warts and surrounding skin of the subject with said treatment solution;
       applying a styptic to the wet genital warts and surrounding skin, wherein said styptic comprises a styptic pencil;
       air drying the wet genital warts and surrounding skin;
       waiting a period time, wherein said period of time is between about three days and about four days;
       removing an outermost layer of skin on said genital warts; and
   (iii) repeating said treatment application for a duration of time, wherein said duration of time is between about two weeks and about four weeks.

* * * * *